United States Patent [19]

Madison et al.

[11] Patent Number: 4,931,563

[45] Date of Patent: Jun. 5, 1990

[54] OLEUM SULFONATION OF PHENYL QUATERNARY ALKYL AMMONIUM AND PHOSPHONIUM CARBONATE ESTERS

[75] Inventors: Stephen A. Madison; Leonora M. Ilardi, both of Valley Cottage, N.Y.

[73] Assignee: Lever Brothers Company, New York, N.Y.

[21] Appl. No.: 272,143

[22] Filed: Nov. 16, 1988

[51] Int. Cl.[5] .................. C07D 211/42; C07D 211/46; C07C 143/26

[52] U.S. Cl. .................................... 546/222; 544/158; 546/301; 546/342; 548/551; 548/556; 548/573; 558/270; 558/271

[58] Field of Search ................. 558/271, 270; 546/222, 546/301, 342, 383, 384, 399; 544/158; 548/551, 556, 573

[56] References Cited

U.S. PATENT DOCUMENTS

| | | | |
|---|---|---|---|
| 3,987,113 | 10/1976 | Sasaki et al. | 558/271 X |
| 4,751,015 | 6/1988 | Humphreys et al. | 252/99 |
| 4,788,316 | 11/1988 | Thornthwaite et al. | 558/268 |
| 4,818,426 | 4/1989 | Humphreys et al. | 558/271 X |

OTHER PUBLICATIONS

"Studies on the Nitration of m-Cresol. A New Selective Method for the Preparation of 3-Methyl-6-nitrophenol", Sasaki et al. Institute for Biological Science, Sumitomo Chemical Co., Ltd., 1976.

*Primary Examiner*—Mary C. Lee
*Assistant Examiner*—Fiona T. Powers
*Attorney, Agent, or Firm*—Milton L. Honig

[57] ABSTRACT

A process is provided for obtaining sulfophenyl quarternary ammonium or phosphonium substituted carbonic acid esters. The important step in this process involves reacting a phenyl quaternary ammonium or phosphonium substituted carbonic ester with oleum that contains from 0.5 to 33% sulfur trioxide. Amounts in excess of 33% sulfur trioxide lead to increased reaction times and, eventually, unacceptable product conversons.

14 Claims, No Drawings

OLEUM SULFONATION OF PHENYL QUATERNARY ALKYL AMMONIUM AND PHOSPHONIUM CARBONATE ESTERS

BACKGROUND OF THE INVENTION

1. Field of the Invention

The invention relates to a process for preparing sulfonated phenyl carbonic acid esters having a quaternary group which esters are useful as bleach precursors in detergent compositions.

2. The Prior Art

Detergent compositions that rely upon sodium perborate as a bleach normally require a precursor to activate the oxygen-releasing compound where wash-water temperatures are below 60° C. A recently issued patent, U.S. No. 4,751,015 (Humphreys et al.), reported an exceptionally effective bleach precursor family of compounds identified as quaternary ammonium or phosphonium substituted peroxy carbonic acid esters. These precursors were reported synthesized in a two-step procedure. Illustrative is 2-(N,N,N-trimethylammonium)ethyl sodium 4-sulphophenyl carbonate chloride (SPCC) which was synthesized by first preparing choline chloroformate chloride through reaction of phosgene with choline chloride in a chloroform solution. The choline chloroformate chloride was then isolated as a crystalline solid. In a second step, the solid choline chloroformate chloride was added to an aqueous solution of sodium 4-phenol sulfonate containing an equimolar amount sodium hydroxide.

A number of problems are associated with this process. For instance, there are handling problems with choline chloroformate chloride, a highly hygroscopic material. Spontaneous crystallization of the chloroformate from solution has been noted. This presents a challenge in commercial production to avoid pipeline constriction. Furthermore, yields of the final product, SPCC, are variable, sometimes being even quite poor (40–85%). Instability of the final product is a still further problem.

Final bleach precursor product, e.g. SPCC, resulting from this process normally contains a very substantial amount of sodium chloride. This by-product is undesirable for several reasons. Sodium chloride promotes corrosion of certain metallic parts of washing machines. Further, sodium chloride takes up valuable space within a detergent formulation without contributing any useful functionality.

Consequently, it is an object of the present invention to provide an improved process for the synthesis of quaternary ammonium or phosphonium substituted carbonic acid esters.

A more specific object of the present invention is to provide an improved process for obtaining the aforementioned carbonic acid esters which limits the amount of sodium chloride present in the final product.

A further object of the present invention is to provide a synthesis of carbonic acid esters that results in a high and relatively reproducible product yield.

SUMMARY OF THE INVENTION

A process is provided for preparation of sulfophenyl quaternary ammonium and phosphonium carbonate esters of the formula:

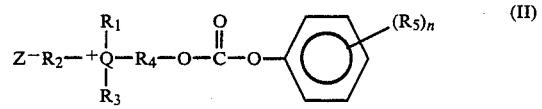

wherein:

- $R_1$, $R_2$ and $R_3$ are each a radical selected from the group consisting of alkyl, alkenyl, alkynyl, cycloalkyl, cycloalkenyl, alkaryl, aryl, phenyl, hydroxyalkyl, and polyoxyalkylene;
- or two or more of $R_1$, $R_2$, and $R_3$ together form an alkyl substituted or unsubstituted nitrogen-containing heterocyclic ring system;
- or at least one of $R_1$, $R_2$, and $R_3$ is attached to $R_4$ to form an alkyl substituted or unsubstituted nitrogen-containing heterocyclic ring system;
- $R_4$ is selected from a bridging group consisting of alkylene, cycloalkylene, alkylenephenylene, phenylene, arylene, and polyalkoxylene; and wherein the bridging group can be unsubstituted or substituted with $C_1$–$C_{20}$ atoms selected from alkyl, alkenyl, benzyl, phenyl and aryl radicals;
- Q is nitrogen or phosphorous;
- $R_5$ is $C_1$–$C_{12}$ alkyl, $C_1$–$C_{12}$ alkoxy, carboxy, hydroxy, $C_1$–$C_{12}$ alkyl carboxy group and mixtures thereof; and
- n ranges from 0 to 4;

comprising the steps of:

(i) reacting a phenyl quaternary ammonium or phosphonium carbonate of the formula:

$$Z^- R_2 - \overset{R_1}{\underset{R_3}{+Q}} - R_4 - O - \overset{O}{\underset{}{C}} - O - \underset{}{\bigcirc}(R_5)_n \quad (II)$$

wherein $Z^-$ is a monovalent or multivalent anion leading to charge neutrality when combined in the appropriate ratio with $Q^+$; with a sulfonation reagent consisting of oleum wherein the percent sulfur trioxide ranges from about 0.5 up to 33%; and (ii) recovering from the reaction said quaternary ammonium or phosphonium carbonate ester of formula I.

DETAILED DESCRIPTION OF THE INVENTION

The present invention describes an oleum sulfonation process that provides sulfophenyl esters of quaternary ammonium or phosphonium substituted carbonic acids containing no more than small amounts of halide counterion. These sulfophenyl esters are useful adjuncts in fabrics washing powders. They provide excellent low temperature stain bleaching when formulated with peroxygen compounds such as those of sodium perborate or sodium percarbonate.

There are a whole variety of sulfonation agents known in the art. These include sulfur trioxide, chlorosulfonic acid and concentrated sulfuric acid. Each of these present problems in that they require large stoichiometric excesses to achieve good yields of the subject carbonic acid esters. Although not wishing to be bound by any theory, it is believed the excess sulfonation agent is required because of the normally present chloride counterion associated with the reactant quaternary ammonium or phosphonium substituted carbonic acid ester (II). Halide ion reacts with the electrophilic sulfonating agent and is now believed to be the cause in reducing its reactivity. This is represented in equation 1 and 2 for the cases of sulfur trioxide and chlorosulfonic acid, respectively.

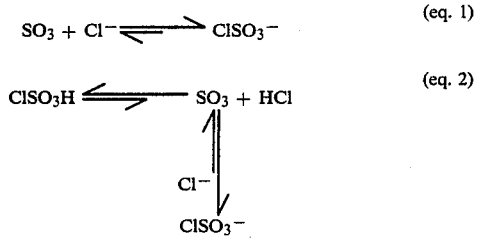

Only after the addition of a second equivalent of sulfur trioxide according to equation 1 does the reaction of the present invention proceed to completion. Further, the fact that the reaction must be performed in an organic solvent, e.g. 1,2-dichloroethane, at reflux means that work-up of the product involves the extra step of solvent stripping. Most importantly, since the chloride ion is still bound with the first equivalent of sulfur trioxide, neutralization of the reaction mixture results in sodium chloride in the finished product.

With concentrated sulfuric acid at room temperature, the sulfonation reaction was not observed. When the temperature of the reaction medium was raised to 90° C., only hydrolysis was observed. Sulfophenol was the only sulfonated product found. Presumably, the activity of the hydronium ion in concentrated (95–100%) sulfuric acid was high enough to promote acid catalyzed hydrolysis.

According to the present invention, it has been found that the strength of the oleum is an important factor in determining the reaction time for quantitative conversion to the sulfonated product. As the mole fraction of sulfur trioxide in oleum increases the rate of reaction decreases. Thus, it has been found that the oleum strength in terms of percent sulfur trioxide must range from about 0.5 up to 33%, preferably no higher than 25%. Amounts greater than 33% result in a very substantial, unacceptable increase in reaction time.

This unexpected result is believed to be due to the decrease of the $H_2SO_4/SO_3$ ratio as the oleum strength increases. In other words, the actual sulfonating agent in this reaction is sulfuric acid whereas the sulfur trioxide serves only to bind the chloride counterion. Further, as the sulfuric acid sulfonates the phenyl ring, water is produced as a by-product and, instead of promoting hydrolysis of the quaternary alkyl ammonium sulfophenyl carbonate product, the water reacts with the chlorosulfate anion to form hydrogen chloride and bisulfate.

Although the sulfonation reaction is quite facile at lower oleum strength, an advantage in performing the reaction at the higher oleum strength is that the amount of sodium sulfate formed on neutralization is minimized. With less sodium sulfate in the finished product, one has even more flexibility in terms of formulating the material into a finished fabrics washing powder.

Advantageously, the reaction is conducted at a temperature of less than 200° C., preferably between 40° C. and 150° C., optimally between 75° C. and 125° C.

Although phosphonium groups where Q is phosphorous is within the scope of this invention, for economic reasons it is most preferred that Q be nitrogen. Furthermore, the precursor should preferably contain a quaternary ammonium carbon surrounded by $R_1$, $R_2$ and $R_3$ each the same or different and having $C_1$–$C_{20}$ atom radicals selected from the group consisting of alkyl, alkylaryl, benzyl, hydroxyalkyl, heterocyclic rings containing the quaternary nitrogen groups where $R_1$ and $R_4$ or $R_1$ and $R_2$ are joined together, and mixtures of groups thereof.

In particular, it is desirable that $R_1$ be a short-chain $C_1$–$C_4$ alkyl radical, preferably methyl, while $R_2$ and $R_3$ be a longer chain $C_7$–$C_{20}$ alkyl or alkylaryl, such as stearyl, lauryl, or benzyl group. With regard to the $R_4$ bridge between the quaternary nitrogen and carbonate groups, it is desirable that $R_4$ be a bridging group selected from $C_2$–$C_{20}$ alkylene, $C_6$–$C_{12}$ phenylene, $C_5$–$C_{20}$ cycloalkylene, and $C_8$–$C_{20}$ alkylenephenylene groups. Preferably, the alkylene groups should have 2 carbons atoms. Further, the bridging group can be unsubstituted or substituted with $C_1$–$C_{20}$ alkyl, alkenyl, benzyl, phenyl and aryl radicals.

Within the context of this invention, there may be compounds having the general structure (I) where $R_1$ and $R_4$ together or $R_1$ and $R_2$ together form an alkyl substituted or unsubstituted nitrogen-containing heterocyclic ring system. Representative of these systems are rings defining pyridine, morpholine, pyrrolidine, piperidine and piperazine.

More specific compounds are listed in U.S. Pat. No. 4,751,015 which is herein incorporated by reference.

The process is described generally as comprising the steps of:
 (i) reacting a phenyl quaternary ammonium or phosphonium carbonate of the formula:

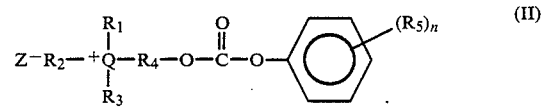

wherein $Z^-$ is a monovalent or multivalent anion leading to charge neutrality when combined in the appropriate ratio with $Q^+$; with a sulfonation reagent consisting of oleum wherein the percent sulfur trioxide ranges from about 0.5 up to 33%; and
 (ii) recovering from the reaction said quaternary ammonium or phosphonium carbonate ester of formula I.

The following examples will more fully illustrate the embodiments of this invention. All parts, percentages and proportions referred to herein and in the appended claims are by weight unless otherwise illustrated.

EXAMPLE 1

A typical oleum sulfonation was performed as follows. In a three-necked 100 ml round bottom flask equipped with a mechanical stirrer and drying tube were placed 12.3 gms (3.08 gms, 38.5 mmoles of "free" sulfur trioxide) of 25% oleum. This reaction vessel was chilled in an ice bath. Thereinto was rapidly added 10.0 gms (38.5 mmoles) of cholyl phenyl carbonate chloride. A highly viscous beige-colored solution resulted. The solution was heated in an oil bath at 100° C. for 70 minutes. During the reaction, hydrogen chloride outgassing was noted as soon as the reaction solution was heated. NMR analysis of the reaction mixture revealed quantitative conversion to sulfonated product at the end of the heating period.

To the above solution was added 12 ml of water so as to decrease the viscosity. Anhydrous sodium carbonate was slowly added to the reaction solution until the pH rose to 4–5. The resultant thick slurry was allowed to dry in air. The solid product was 44% active, the remainder being sodium sulfate and sodium chloride. Residual sodium chloride was 15% of the theoretical amount as determined by a potentiometric chloride titration. Yield of 2-(N,N,N-trimethylammonium)ethyl 4-sulfophenyl carbonate was 95%.

EXAMPLE 2

Illustrated herein is the effect of varying the oleum strength used for the sulfonation reaction. All of the experients were run in accordance with the reaction as outlined in Example 1. Each of the entries in the Table were calculated for 90% conversion.

TABLE I

Relationship of Oleum Strength with Reaction Time

| Oleum Strength % $SO_3$ | Time (Min.) |
|---|---|
| 5 | <1 |
| 10 | <1 |
| 15 | <1 |
| 21 | 5 |
| 26 | 60 |
| 28 | 75 |
| 30 | 120 |
| 33 | 210 |
| 46 | 2520* |

*maximum conversion observed 75%

Evident from the Table is that at 26% oleum strength there is greater than a ten-fold increase in reaction time relative to the 21% oleum strength level.

The foregoing description and examples illustrate selected embodiments of the present invention. In light thereof, various modifications will be suggested to one skilled in the art, all of which are within the spirit and purview of this invention.

What is claimed is:

1. A process for preparation of sulfophenyl quaternary ammonium and phosphonium carbonate esters of the formula:

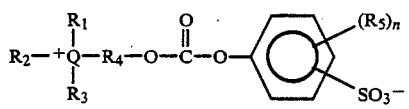 (I)

wherein:

$R_1$, $R_2$ and $R_3$ are each a radical selected from the group consisting of alkyl, alkenyl, alkynyl, cycloalkyl, cycloalkenyl, alkaryl, aryl, phenyl, hydroxyalkyl, and polyoxyalkylene;

or two or more of $R_1$, $R_2$, and $R_3$ together form an alkyl substituted or unsubstituted nitrogen-containing heterocyclic ring system;

or at least one of $R_1$, $R_2$, and $R_3$ is attached to $R_4$ to form an alkyl substituted or unsubstituted nitrogen-containing heterocyclic ring system;

$R_4$ is selected from a bridging group consisting of alkylene, cycloalkylene, alkylenephenylene, phenylene, arylene, and polyalkoxylene; and wherein the bridging group can be unsubstituted or substituted with $C_1$–$C_{20}$ atoms selected from alkyl, alkenyl, benzyl, phenyl and aryl radicals;

Q is nitrogen or phosphorous;

$R_5$ is $C_1$–$C_{12}$ alkyl, $C_1$–$C_{12}$ alkoxy, carboxy, hydroxy, $C_1$–$C_{12}$ alkyl carboxy group and mixtures thereof; and n ranges from 0 to 4;

comprising the steps of:

(i) reacting a phenyl quaternary ammonium or phosphonium carbonate of the formula:

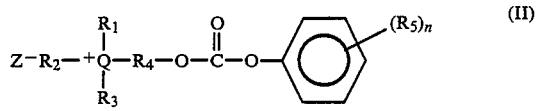 (II)

wherein $Z^-$ is a monovalent or multivalent anion leading to charge neutrality when combined in the appropriate ratio with $Q^+$; with a sulfonation reagent consisting of oleum wherein the percent sulfur trioxide ranges from about 0.5 up to 33%; and (ii) recovering from the reaction said quaternary ammonium or phosphonium carbonate ester of formula I.

2. A process according to claim 1 wherein Q is nitrogen and $R_1$, $R_2$ and $R_3$ are each the same or different and selected from $C_1$–$C_{20}$ atom radicals selected from the group consisting of alkyl, alkylaryl, benzyl, hydroxyalkyl, and heterocyclic rings containing the quaternary nitrogen where $R_1$ and $R_4$ or $R_1$ and $R_2$ are joined together, and mixtures of groups thereof.

3. A process according to claim 2 wherein $R_1$ is selected from short-chain $C_1$–$C_4$ alkyl radicals.

4. A process according to claim 2 wherein $R_2$ and $R_3$ are each a longer chain $C_7$–$C_{20}$ alkyl or alkylaryl radical.

5. A process according to claim 4 wherein said longer chain radical is selected from the group consisting of benzyl, lauryl and stearyl groups.

6. A process according to claim 1 wherein $R_4$ is selected from a bridging group consisting of $C_2$–$C_{20}$ alkylene, $C_6$–$C_{12}$ phenylene, $C_5$–$C_{20}$ cycloalkylene, and $C_8$–$C_{20}$ alkylphenylene groups.

7. A process according to claim 6 wherein the $R_4$ bridging group is a $C_2$–$C_6$ alkylene or $C_6$–$C_{12}$ phenylene group.

8. A process according to claim 2 wherein said heterocyclic ring is selected from pyridine, morpholine, pyrrolidone, piperidine and piperazine.

9. A process according to claim 1 wherein the ester product is 2-(N,N,N-trimethylammonium)ethyl 4-sulfophenyl carbonate salt.

10. A process according to claim 1 wherein the ester product is 2-(N-benzyl-N,N-dimethylammonium)ethyl 4-sulfophenyl carbonate salt.

11. A process according to claim 1 wherein the ester product is 2-(N-butyl-N,N-dimethylammonium)ethyl 4-sulfophenyl carbonate salt.

12. A process according to claim 1 wherein the ester product is 2-[4-(N,N,N-trimethylammonium)phenyl]ethyl 4-sulfophenyl carbonate salt.

13. A process according to claim 1 wherein the ester product is 3-(1,1-dimethylpiperidinium) 4-sulfophenyl carbonate salt.

14. A process according to claim 1 wherein the ester product is 4-(1,1-dimethylpiperidinium) 4-sulfophenyl carbonate salt.

* * * * *